United States Patent
Higa et al.

(10) Patent No.: US 10,772,976 B2
(45) Date of Patent: Sep. 15, 2020

(54) METHOD FOR DETECTING AFP

(71) Applicant: SYSMEX CORPORATION, Kobe-shi, Hyogo (JP)

(72) Inventors: Yukiko Higa, Tokyo (JP); Masatoshi Suganuma, Kawasaki (JP); Yuriko Egashira, Tokorozawa (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 200 days.

(21) Appl. No.: 15/789,569

(22) Filed: Oct. 20, 2017

(65) Prior Publication Data
US 2018/0110889 A1    Apr. 26, 2018

(30) Foreign Application Priority Data

Oct. 24, 2016   (JP) ................. 2016-207789

(51) Int. Cl.
| | |
|---|---|
| *G01N 33/53* | (2006.01) |
| *G01N 33/68* | (2006.01) |
| *C07K 1/107* | (2006.01) |
| *C07K 16/18* | (2006.01) |
| *A61K 51/10* | (2006.01) |
| *C07K 16/44* | (2006.01) |
| *C07K 16/30* | (2006.01) |
| *A61K 39/395* | (2006.01) |
| *A61K 39/00* | (2006.01) |

(52) U.S. Cl.
CPC ............ *A61K 51/10* (2013.01); *A61K 39/395* (2013.01); *C07K 1/1077* (2013.01); *C07K 16/18* (2013.01); *C07K 16/30* (2013.01); *C07K 16/44* (2013.01); *G01N 33/689* (2013.01); *A61K 2039/505* (2013.01); *C07K 2317/34* (2013.01); *G01N 33/6854* (2013.01); *G01N 2333/471* (2013.01); *G01N 2400/02* (2013.01); *G01N 2400/38* (2013.01)

(58) Field of Classification Search
CPC ............... C07K 16/18; C07K 16/3076; C07K 2317/34; C07K 2317/565; G01N 33/6854; G01N 2333/471; G01N 2400/02; G01N 2400/38
See application file for complete search history.

(56) References Cited

U.S. PATENT DOCUMENTS

2016/0245823 A1*   8/2016   Liu .................. G01N 33/6878

FOREIGN PATENT DOCUMENTS

| EP | 1677112 A1 * | 7/2006 | ......... G01N 33/5306 |
|---|---|---|---|
| JP | 60-67431 A | 4/1985 | |
| JP | 63-307900 A | 12/1988 | |

OTHER PUBLICATIONS

Paul, Fundamental Immunology, 3rd Edition, 1993, pp. 292-295.*
Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Padlan, Advances in Protein Chemistry, 1996, 49:57-133.*
Berglund et al. (Berglund et al, Protein Science, 2008, 17:606-613.*

* cited by examiner

*Primary Examiner* — Hong Sang
(74) *Attorney, Agent, or Firm* — Sughrue Mion, PLLC

(57) ABSTRACT

Disclosed is a monoclonal antibody reactive with a glycopeptide shown in (a), and

[Chemical Formula 1]

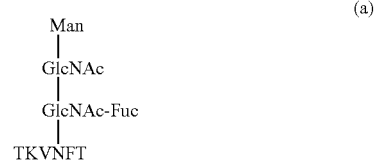

not reactive with a glycopeptide shown in (b)

[Chemical Formula 2]

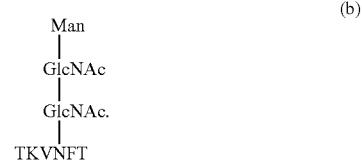

4 Claims, 6 Drawing Sheets
Specification includes a Sequence Listing.

FIG. 7

| Peptide chain length | Sugar chain length | Structure |
|---|---|---|
| 16a.a. | 7 | 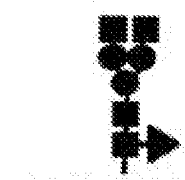 ATKVNFTEAQKAALDV |

FIG. 8

| Positive antigen (Glycopeptide A) | Negative antigen (Non-fucosylated glycopeptide A) |
|---|---|
|  ATKVNFTEAQKAALDV |  ATKVNFTEAQKAALDV |

FIG. 9

| | Positive glycopeptide (Fuc +) | Negative glycopeptide (Fuc -) |
|---|---|---|
| [1] 7a.a. trisaccharide |  (BSA)~PEG4~[GTKVNFT] | 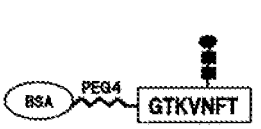 (BSA)~PEG4~[GTKVNFT] |
| [2] 10a.a. trisaccharide |  (BSA)~[GTKVNFTEIQ] | 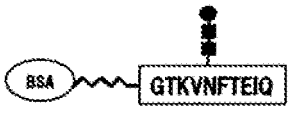 (BSA)~[GTKVNFTEIQ] |
| [3] 10a.a. heptasaccharide |  (BSA)~[GTKVNFTEIQ] |  (BSA)~[GTKVNFTEIQ] |
| [4] 16a.a. heptasaccharide |  (BSA)~[ATKVNFTEAQKAALDV] | 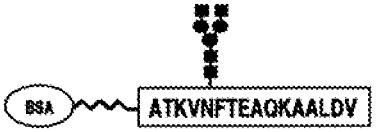 (BSA)~[ATKVNFTEAQKAALDV] |

METHOD FOR DETECTING AFP

CROSS REFERENCE TO RELATED APPLICATIONS

This application claims priority from prior Japanese Patent Application No. 2016-207789, filed on Oct. 24, 2016, entitled "Monoclonal antibody reactive with glycopeptide and uses thereof", the entire contents of which are incorporated herein by reference.

TECHNICAL FIELD

The present invention relates to method for detecting AFP using a monoclonal antibody reactive with a glycopeptide.

BACKGROUND

It is said that α-fetoprotein (AFT) (LCA-binding AFP) that binds to lentil lectin (LCA) increases in biological samples when hepatitis/liver cirrhosis changes to liver cancer. An antibody for detecting LCA-binding AFP is described in JP S63-307900 A. It is described that the antibody of JP S63-307900 A shows reactivity to the binding AFP and shows no reactivity with LCA non-binding AFP.

In JP S63-307900 A, it is described that fucose exists in the sugar chain of AFP to which LCA binds. The fraction of AFP that binds to lentil lectin in a biological sample is called AFP-L3 fraction. The AFP-L3 fraction is composed of fucosylated AFP (AFP in which core fucose (fucose which is bound in α-1,6 linkage to N-acetylglucosamine (GlcNAc) at the reducing end of N-type sugar chain) is added to the asparagine residue of AFP).

In the examples of JP S63-307900 A, antibodies which bind to LCA-binding AFP (AFP-LCA-R) and do not bind to LCA non-binding AFP (AFP-LCA-NR) have been acquired (see Example 1, FIG. 7, FIG. 1). However, the epitope of this antibody is unknown. In the examples, LCA-binding and non-binding properties are said to be caused by the presence or absence of fucose as described above, and the binding affinity to antigen may depend on the fucose moiety independent of the sequence of the peptide moiety. In that case, the antibody may non-specifically bind not only to AFP but also to proteins having other fucose. Therefore, development of a monoclonal antibody having epitope on both the fucose portion of the glycopeptide and the amino acid of the peptide portion is desired.

SUMMARY OF THE INVENTION

The scope of the present invention is defined solely by the appended claims, and is not affected to any degree by the statements within this summary.

A first aspect of the present invention provides a method for detecting fucosylated AFP using an antibody, wherein the antibody binds to a glycopeptide (a) (SEQ ID NO: 13),

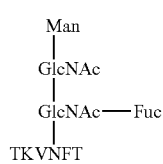

(a)

and
does not bind to a glycopeptide (b) (SEQ ID NO: 14)

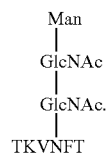

(b)

A second aspect of the present invention provides a monoclonal antibody which binds to a glycopeptide (a) (SEQ ID NO: 13),

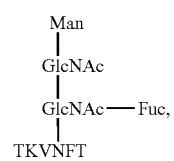

(a)

and
does not bind to a glycopeptide (b)) (SEQ ID NO: 14)

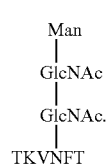

(b)

A third aspect of the present invention provides hybridoma with international deposit number NITE ABP-02349 or NITE ABP-02350.

BRIEF DESCRIPTION OF THE DRAWINGS

FIG. 7 is a table showing the structure of glycopeptide A. The circle represents mannose, the square represents N-acetylglucosamine, and the triangle represents fucose. The N-terminal of the glycopeptide is KLH-PEG 4, and the C-terminal is amidated.

FIG. 8 is a table showing the structures of glycopeptide A and non-fucosylated glycopeptide A. The circle represents mannose, the square represents N-acetylglucosamine, and the triangle represents fucose. The N-terminal of the glycopeptide is KLH-PEG 4, and the C-terminal is amidated.

FIG. 9 is a table showing multiple fucosylated and non-fucosylated glycopeptides.

DETAILED DESCRIPTION OF THE PREFERRED EMBODIMENTS

Figure 1:
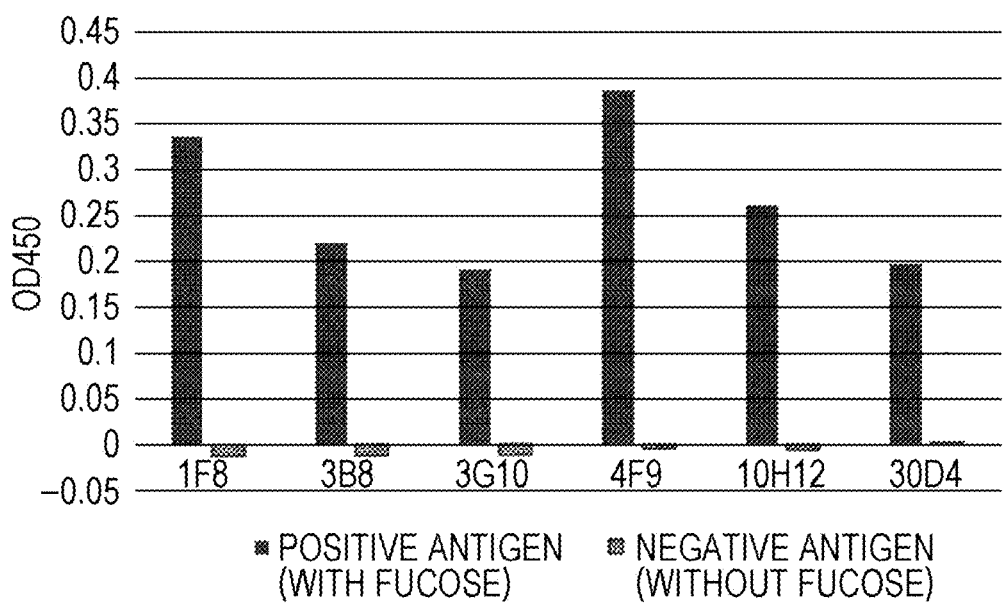
FIG. 1 is a diagram showing the result of performing antigen solid phase ELISA using positive antigen (glycopeptide A) or negative antigen (non-fucosylated glycopeptide A) shown in FIG. 8 as an antigen using culture supernatant of antibody-producing cells.

The antibody of the present embodiment may exhibit specificity in a measurement system using a biological sample or the like in which the antibody of the present embodiment is used. For example, even if the antibody nonspecifically binds to a substance not contained in a biological sample, the effect of the present disclosure is exerted when the specificity is exhibited in the environment in which the antibody of the present embodiment is normally used. Specifically, when a substance in a blood sample such as whole blood, serum, or plasma is detected by ELISA, it is only necessary to show specificity in ELISA measurement system, and the antibody may bind to a substance which is not normally contained in a blood sample or an ELISA reagent.

The antibody of the present embodiment is a monoclonal antibody reactive with a glycopeptide (SEQ ID NO: 13) shown in (a), and

[Chemical Formula 3]

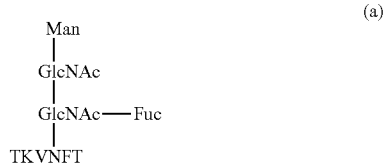

(a)

not reactive with a glycopeptide (SEQ ID NO: 14) shown in (b)

[Chemical Formula 4]

(b)

The phrase that the antibody of the present embodiment "reactive with a glycopeptide" herein refers that a glycopeptide and the antibody are bound by antigen-antibody reaction.

Further, the antibody reactive with fucosylated AFP is preferred.

Furthermore, the antibody can bind to denatured fucosylated AFP that has been pretreated with a denaturant such as SDS or heat. The SDS concentration (hereinafter, referred to as "pretreatment SDS concentration") for sufficiently denaturing the fucosylated AFP when a solution containing SDS is used as a pretreatment is not particularly limited, but is preferably 0.03 mass/mass % (hereinafter, simply referred to as "%") or more, and more preferably 0.25%. Meanwhile, when the denaturant is excessively contained in the antigen-antibody reaction, the antibody may also be denatured to adversely affect the antigen-antibody reaction, thus it is preferable to lower the denaturant concentration by dilution or the like. When a solution containing SDS is used as a denaturant, the SDS concentration in the antigen-antibody reaction (hereinafter, referred to as "final SDS concentration") is not particularly limited, but is preferably 0.025% or less, and more preferably 0.0015%.

The phrase that the antibody of the present embodiment "reactive with fucosylated AFP" herein refers that fucosylated AFP and the antibody are bound by antigen-antibody reaction. The fucosylated AFP may be either recombinant or natural. Natural fucosylated AFP is, for example, AFP present in human blood. The sequence of human AFP is registered, for example, in GenBank Accession No. NM_001134 and has the amino acid sequence of SEQ ID NO: 26.

Further, the antibody reactive with fucosylated AFP denatured in the presence of SDS and DTT is preferred. The denaturation conditions are a reaction at room temperature (25° C.), in the presence of 2% SDS and 50 mM DTT.

Further, the antibody unreactive with non-fucosylated AFP denatured in the presence of SDS and DTT is preferred. The denaturation conditions are a reaction at room temperature (25° C.), in the presence of 2% SDS and 50 mM DTT.

The following are examples of the CDR of the antibody of the present embodiment.

<CDR-A>

The CDR of the heavy chain includes the amino acid sequence shown in SEQ ID NO: 1, the amino acid sequence shown in SEQ ID NO: 2, and the amino acid sequence shown in SEQ ID NO: 3. The CDR of the light chain includes the amino acid sequence shown in SEQ ID NO: 4, the amino acid sequence shown in SEQ ID NO: 5, and the amino acid sequence shown in SEQ ID NO: 6.

<CDR-B>

The CDR of the heavy chain comprises the amino acid sequence shown in SEQ ID NO: 7, the amino acid sequence shown in SEQ ID NO: 8, and the amino acid sequence shown in SEQ ID NO: 9. The CDR of the light chain comprises the amino acid sequence shown in SEQ ID NO: 10, the amino acid sequence shown in SEQ ID NO: 11, and the amino acid sequence shown in SEQ ID NO: 12.

Hybridomas that produce the antibodies of the present embodiment having CDR-A and CDR-B as the CDRs were named S4-1F8 and S4-4F9, respectively, and were internationally deposited with the Patent Microorganisms Depositary, Biological Resource Center, National Institute of Technology and Evaluation (#122, 2-5-8 Kazusakamatari, Kisarazu-shi, Chiba 292-0818, Japan) on Sep. 8, 2016, as NITE ABP-02349 and NITE ABP-02350.

The antibody of the present embodiment can be obtained by a method including a step of immunizing an animal with a glycopeptide antigen (SEQ ID NO: 15) having the following structure.

[Chemical Formula 5]

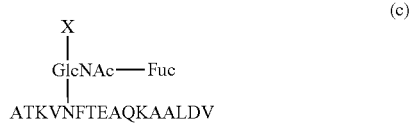

(c)

X is an arbitrary sugar chain and is not generally particularly limited as long as it is a sugar chain which is bound to a glycoprotein or a glycopeptide.

A biopolymer such as KLH or BSA may be bound to the N-terminus of the glycopeptide antigen via PEG or the like. The C-terminus of these glycopeptide antigens may be amidated or the like. As a method of binding the biopolymer to the N-terminus, a known method can be used. A known method can be used also for amidation of the C-terminus.

In the step of immunizing an animal with a glycopeptide antigen, a step of immunizing an animal in a known method for producing monoclonal antibodies can be used. Examples of the method for producing monoclonal antibodies include mouse spleen method, mouse iliac lymph node method (see JP 4098796 B2), and the like.

Animals to be immunized are not particularly limited, and may be appropriately selected from non-human animals according to the method for producing monoclonal antibodies.

Specifically, when the mouse spleen method is used as the method for producing monoclonal antibodies, animals may be immunized according to a known method.

After immunizing an animal, the antibody of the present embodiment may be obtained by preparing and selecting hybridomas, and the like, according to a known method.

When selecting hybridomas, a glycopeptide as an antigen, a glycopeptide as an antigen from which core fucose was removed, one containing a part of amino acid residues of a glycopeptide as an antigen, fucosylated AFP denatured in the presence of SDS and DTT, non-fucosylated AFP denatured in the presence of SDS and DTT, glycopeptide or glycoprotein (e.g., fucosylated ALP) having a core fucose and also having a polypeptide with an amino acid sequence different from AFP or the like may be appropriately used as a positive antigen or a negative antigen.

As criteria for selecting hybridomas, for example, in the case of using ELISA, the difference in OD450 values between the positive antigen and the negative antigen is 0.05 or more, and OD450 value of the negative antigen is 0.05 or less.

The isotype of the antibody of the present embodiment is not particularly limited. The antibody of the present embodiment also includes a fragment such as a peptide containing $F(ab')_2$, Fab', Fab, CDR.

The antibody of the present embodiment may be labeled such as biotinylated, ALP-converted, or the like.

The antibody of the present embodiment has the above properties, thus reacts with fucosylated AFP and does not react with non-fucosylated AFP. Therefore, for example, the antibody of the present embodiment can measure fucosylated AFP in a biological sample.

Examples of the biological samples include whole blood, serum and plasma collected from a subject and the like. This biological sample may be subjected to a pretreatment such as centrifugal separation or denaturation treatment. The biological sample is preferably subjected to denaturation treatment. The conditions for the denaturation treatment are reactions at ordinary temperature (25° C.), in the presence of 2% SDS and 50 mM DTT.

In order to measure fucosylated AFP using the antibody of the present embodiment, a known immunological measurement method can be used. Examples of the immunoassay include enzyme-linked immunosorbent assay (ELISA method), immune complex metastasis measurement method (see JP H01-254868 A), immunoturbidimetry, immunochromatography, latex agglutination method, and the like. As an example of a measurement step, the case where the fucosylated AFP concentration in a biological sample is measured by a sandwich ELISA method will be described below.

First, a complex containing an antibody for capturing fucosylated AFP (hereinafter, also referred to as "capture antibody") in a biological sample, an antibody for detecting fucosylated AFP (hereinafter, also referred to as "detection antibody") and fucosylated AFP is formed on a solid phase. When fucosylated AFP is contained in a biological sample, this complex can be formed by mixing the biological sample, the capture antibody and the detection antibody. Then, a solution containing the complex is brought into contact with a solid phase capable of capturing the capture antibody, whereby the complex can be formed on the solid phase. Alternatively, a solid phase preliminarily immobilized with the capture antibody may be used. That is, a solid phase immobilized with the capture antibody, the biological sample, and the detection antibody are brought into contact with each other, whereby the complex can be formed on the solid phase. The antibody of the present embodiment can be used for at least one of the capture antibody and the detection antibody.

The mode of immobilization of the capture antibody on the solid phase is not particularly limited. For example, the capture antibody and the solid phase may be bound directly, or the capture antibody and the solid phase may be indirectly bound via another substance. Examples of the direct bond include physical adsorption and the like. Examples of the indirect bond include a bond via a combination of biotin and avidin or streptavidin (hereinafter, also referred to as "avidins"). In this case, by preliminarily modifying the capture antibody with biotin and previously binding avidins to the solid phase, the capture antibody and the solid phase can be indirectly bound via the bond between the biotin and the avidins.

The material of the solid phase is not particularly limited, and it can be selected from, for example, organic polymer compounds, inorganic compounds, biopolymers, and the like. Examples of the organic polymer compound include latex, polystyrene, polypropylene, and the like. Examples of the inorganic compound include magnetic bodies (iron oxide, chromium oxide, ferrite, etc.), silica, alumina, glass, and the like. Examples of the biopolymer include insoluble agarose, insoluble dextran, gelatin, cellulose, and the like. Two or more of these may be used in combination. The shape of the solid phase is not particularly limited, and examples thereof include particles, membranes, microplates, microtubes, test tubes, and the like.

The measured value of fucosylated AFP in a biological sample can be acquired by detecting the complex formed on the solid phase by a method known in the art. For example, when an antibody labeled with a labeling substance is used as a detection antibody, the measured value of fucosylated AFP can be acquired by detecting a signal generated by the labeling substance. Alternatively, also when a labeled secondary antibody against the detection antibody is used, the measured value of fucosylated AFP can be acquired in the same manner.

In the present embodiment, it is preferable that the fucosylated AFP is pretreated as described above. When a solution containing SDS is used as a pretreatment, the pretreatment SDS concentration is not particularly limited, but is preferably 0.03% or more, and more preferably 0.25%. In the antigen-antibody reaction, as described above, it is preferable to lower the concentration of the denaturant by dilution or the like. When a solution containing SDS is used as a denaturant, the final SDS concentration is not particularly limited, but is preferably 0.025% or less, and more preferably 0.0015%. In the present embodiment, it is preferable to perform such a treatment to obtain a measured value of fucosylated AFP by reacting the antibody with the fucosylated AFP.

In the present embodiment, B/F (Bound/Free) separation for removing an unreacted free component not forming a complex may be performed between the process of forming the complex and the process of detecting the complex. The unreacted free component refers to a component not constituting a complex. Examples include antibodies not bound to fucosylated AFP, substances (contaminants) other than fucosylated AFP in a biological sample, and the like. The means of B/F separation is not particularly limited, and when the solid phase is a particle, B/F separation can be performed by recovering only the solid phase capturing the complex by centrifugation. When the solid phase is a container such as a microplate or a microtube, B/F separation can be performed by removing a liquid containing an unreacted free component. When the solid phase is a magnetic particle, B/F separation can be performed by aspirating and removing a liquid containing an unreacted free component by a nozzle while magnetically constraining the magnetic particles with a magnet. After removing the unreacted free component, the solid phase capturing the complex may be washed with a suitable aqueous medium such as PBS.

The phrase "detecting a signal" herein includes qualitatively detecting the presence or absence of a signal, quantifying a signal intensity, and semi-quantitatively detecting the intensity of a signal. Semi-quantitative detection means to show the intensity of the signal in stages such as "no signal generated", "weak", "medium", "strong", and the like. In the present embodiment, it is preferable to detect the intensity of a signal quantitatively or semi-quantitatively.

The labeling substance is not particularly limited as long as a detectable signal is generated. For example, it may be a substance which itself generates a signal (hereinafter, also referred to as "signal generating substance") or a substance which catalyzes the reaction of other substances to generate a signal. Examples of the signal generating substance include fluorescent substances, radioactive isotopes, and the like. Examples of the substance that catalyzes the reaction of other substances to generate a detectable signal include enzymes and the like. Examples of the enzymes include alkaline phosphatase, peroxidase, β-galactosidase, luciferase, and the like. Examples of the fluorescent substances include fluorescent dyes such as fluorescein isothiocyanate (FITC), rhodamine and Alexa Fluor (registered trademark), fluorescent proteins such as GFP, and the like. Examples of the radioisotopes include $^{125}I$, $^{14}C$, $^{32}P$, and the like. Among them, an enzyme is preferable as a labeling substance, and alkaline phosphatase and peroxidase are particularly preferable.

Methods for detecting a signal themselves are known in the art. In the present embodiment, a measurement method according to the type of signal derived from the labeling substance may be appropriately selected. For example, when the labeling substance is an enzyme, signals such as light and color generated by reacting a substrate for the enzyme can be measured by using a known apparatus such as a spectrophotometer.

The substrate of the enzyme can be appropriately selected from known substrates according to the type of the enzyme. For example, when alkaline phosphatase is used as the enzyme, examples of the substrate include chemiluminescent substrates such as CDP-Star (registered trademark) (disodium 4-chloro-3-(methoxyspiro[1,2-dioxetane-3,2'-(5'-chloro)tricyclo[3.3.1.13,7]decan]-4-yl)phenyl phosphate) and CSPD (registered trademark) (disodium 3-(4-methoxyspiro[1,2-dioxetane-3,2-(5'-chloro)tricyclo[3.3.1.13,7]decan]-4-yl)phenyl phosphate), and chromogenic substrates such as 5-bromo-4-chloro-3-indolyl phosphate (BCIP), disodium 5-bromo-6-chloro-indolyl phosphate, and p-nitrophenyl phosphate. When peroxidase is used as the enzyme, examples of the substrate include chemiluminescent substrates such as luminol and derivatives thereof, and chromogenic substrates such as 2,2'-azinobis(3-ethylbenzothiazoline-6-ammonium sulfonate) (ABTS), 1,2-phenylenediamine (OPD), and 3,3',5,5'-tetramethylbenzidine (TMB).

When the labeling substance is a radioactive isotope, radiation as a signal can be measured using a known apparatus such as a scintillation counter. When the labeling substance is a fluorescent substance, fluorescence as a signal can be measured using a known apparatus such as a fluorescence microplate reader. The excitation wavelength and the fluorescence wavelength can be appropriately determined according to the type of fluorescent substance used.

The result of detecting a signal may be also used as the measured value of fucosylated AFP. For example, when quantitatively detecting the intensity of a signal, the measured value itself of the signal intensity or the value acquired from the measured value can be used as the measured value of fucosylated AFP. Examples of the value acquired from the measured value of the signal intensity include a value obtained by subtracting the measured value of a negative control sample or the background value from the measured value of fucosylated AFP, and the like. The negative control sample can be appropriately selected, and examples thereof include a biological sample obtained from a healthy subject and the like.

In the present embodiment, the measured value of fucosylated AFP may be acquired for a plurality of standard samples with known fucosylated AFP concentration and a calibration curve showing the relationship between the fucosylated AFP concentration and the measured value of fucosylated AFP may be prepared. The value of the fucosylated AFP concentration in a biological sample can be acquired by applying the measured value of fucosylated AFP acquired from the biological sample to this calibration curve.

In the present embodiment, the fucosylated AFP concentration in a biological sample may be measured by a sandwich ELISA method using a capture antibody immobilized on magnetic particles and a detection antibody labeled with a labeling substance. In this case, measurement may be performed using a commercially available fully automated immunoassay system such as HISCL series (manufactured by Sysmex Corporation).

The antibody of the present embodiment can be used in a fucosylated AFP detection kit. The fucosylated AFP detection kit of the present embodiment includes a capture antibody, a detection antibody, and a solid phase. As the capture antibody or the detection antibody, the antibody of the present embodiment can be used. In the sandwich immunoassay, the antibody of the present embodiment can be used for either the capture antibody or the detection antibody.

In the fucosylated AFP detection kit of the present embodiment, when the labeling substance of the detection antibody is an enzyme, the fucosylated AFP detection kit of the present embodiment may further include a substrate for the enzyme. The forms of the labeling substance and the substrate are not particularly limited, and may be solid (for example, powder, crystal, freeze-dried product, etc.) or liquid (for example, solution, suspension, emulsion, etc.).

The fucosylated AFP detection kit of the present embodiment may further include a pretreatment reagent containing 0.03% or more, and preferably 0.25% of SDS, for pretreating the fucosylated AFP. The reagent is the same as the solution containing 0.03% or more of SDS.

The fucosylated AFP detection kit of the present embodiment may further include a pretreatment solution of a biological sample, a washing liquid of the solid phase, an enzyme reaction terminating agent, a calibrator, and the like.

In the fucosylated AFP detection kit of the present embodiment, the capture antibody, the detection antibody, the solid phase and the like may be stored in a container as appropriate according to the form of the kit or individually packaged. In the fucosylated AFP detection kit of the present embodiment, the capture antibody may be directly bound to the solid phase, or the capture antibody and the solid phase may be indirectly bound via another substance. When the capture antibody and the solid phase are indirectly bound, the capture antibody and the solid phase may be stored in separate containers in the kit of the present embodiment. When the capture antibody and the solid phase are indirectly bound via, for example, biotin and avidin, the capture antibody modified with biotin may be stored in one container, and the solid phase to which the avidin is bound may be stored in another container. The details of the biological sample, the capture antibody, the detection antibody, the solid phase and the like are the same as those described in the description of the measurement method above.

Fucosylated AFP is known to be associated with liver cancer. Therefore, the fucosylated AFP detection kit of the present embodiment can be used for diagnosis of liver cancer.

EXAMPLES

Hereinafter, the present invention will be described in detail by examples, but the present invention is not limited to these examples.

Example 1

Figure 2:
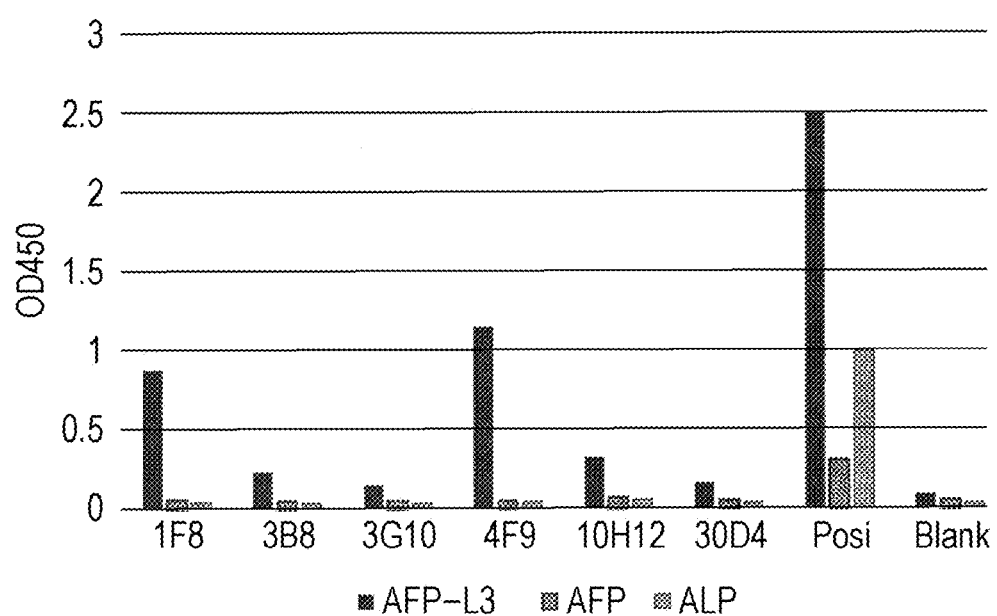
FIG. 2 is a diagram showing the result of performing antigen solid phase ELISA using recombinant AFP-L3, non-fucosylated AFP, and fucosylated ALP as antigens using culture supernatant of antibody-producing cells.

Acquisition of Antibody:
(1) Acquisition of Antibody Group
Hybridomas producing antibody groups were obtained by mouse spleen method. Specifically, glycopeptide A (SEQ ID NO: 16) having the structure shown in FIG. 7 was synthesized, then conjugated with KLH and immunized to three mice. After confirming that the antibody titer increased, lymphocytes were isolated from the spleen of the mouse and fused with myeloma to obtain a hybridoma.
(2) Primary Screening
From the hybridoma obtained in the above (1), by antigen solid phase ELISA using a positive antigen (glycopeptide A) or a negative antigen (non-fucosylated glycopeptide A: SEQ ID NO: 17) described in FIG. 8, wells showing a reaction to the positive antigen and few reaction to the negative antigen were selected. Antigen solid phase ELISA was performed by the following method. The results are shown in FIG. 1.
<Method>
(1) Add 50 μl/well of 1 μg/ml each screening antigen (10 mM phosphate buffer dilution pH 7) to a 96-well plate (nunc Maxisoap/446612) and immobilize the screening antigen at 37° C. for 1 hr.
(2) Wash each well with 300 μl/well PBST×5 times.
(3) Block each well with 100 μl/well 1% BSA-PBS at 4° C. overnight.
(4) Wash each well with 300 μl/well PBST×5 times.
(5) Dilute antibody culture supernatant (primary antibody) 10 times with 1% BSA-PBS, add 50 μl/well, and react at RT for 1 hr.
(6) Wash each well with 300 μl/well PBST×5 times.
(7) Dilute anti mouse IgG-HRP (JIR/715-035-151) and anti mouse IgG Lchain-HRP (JIR/115-035-174) 20,000 times with 1% BSA-PBS, add 50 μl/well, and react at RT for 0.5 hr.
(8) Wash each well with 300 μl/well PBST×5 times.
(9) Add 100 μl/well of HRP chromogenic substrate to develop color.
(10) Add 100 μl/well of a stop solution to stop color development.
(11) Measure OD450.
(3) Secondary Screening
Similarly to the primary screening, antigen solid phase ELISA was performed using the culture supernatant of antibody-producing cells, using AFP-L3, AFP and fucose-modified ALP as antigens. The results are shown in FIG. 2.

From the results of primary screening and secondary screening, antibodies obtained from 1F8 clone and 4F9 clone were selected. Among the clones obtained above, 1F8 clone was named S4-1F8, and was internationally deposited (NITE ABP-02349). 4F9 clone was named S4-4F9, and was internationally deposited (NITE ABP-02350).

Example 2

Confirmation of Specificity of Acquired Antibody:
In order to investigate the reaction specificity of the antibodies S4-1F8 and S4-4F9 each produced from the clones selected in Example 1, the following investigations were carried out.
(1) Antigen Solid Phase ELISA
<Materials>
Solid phase antigen: recombinant AFP-L3, non-fucosylated AFP, fucosylated ALP
Primary antibody: S4-1F8, S4-4F9 (hybridoma culture supernatant)
Secondary antibody: anti mouse IgG-HRP (MEDICAL & BIOLOGICAL LABORATORIES CO., LTD./IM-0817)
<Method>
(1) Add 100 μl/well of 0.5 μg/ml each antigen (10 mM tris buffer dilution pH 7.4) to a 96-well plate (nunc Maxisoap/446612) and immobilize the antigen at RT for 1 hr.
(2) Wash each well with 300 μl/well TBST×5 times.
(3) Block each well with 300 μl/well 1% BSA-TBS at 4° C. overnight.
(4) Wash each well with 300 μl/well TBST×5 times.
(5) Dilute antibody culture supernatant (primary antibody) 10 times with 1% BSA-TBST, add 100 μl/well, and react at RT for 1 hour.
(6) Wash each well with 300 μl/well TBST×5 times.

(7) Dilute the secondary antibody 10,000 times with 1% BSA-TBST, add 100 μl/well, and react at RT for 0.5 hr.

(8) Wash each well with 300 μl/well TBST×5 times.

(9) Add 100 μl/well of HRP chromogenic substrate to develop color.

(10) Add 100 μl/well of a stop solution to stop color development.

(11) Measure OD450.

<Results>

Figure 3:
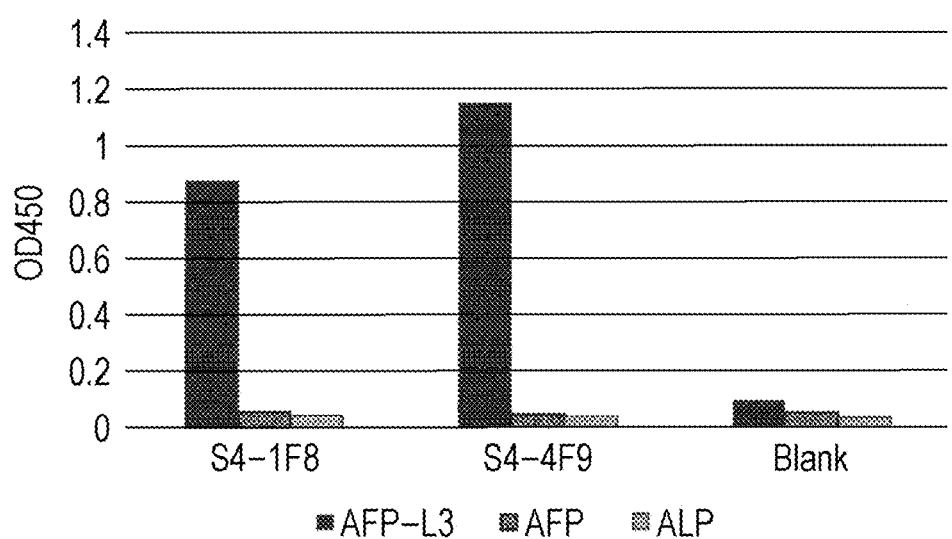
FIG. 3 is a diagram showing the result of performing antigen solid phase ELISA using recombinant AFP-L3, non-fucosylated AFP, and fucosylated ALP as antigens using hybridoma culture supernatant.

The results of antigen solid phase ELISA are shown in FIG. 3. Both S4-1F8 and S4-4F9 showed a reaction specifically to AFP-L3.

(2) Western Blotting

<Materials>

Electrophoresis antigen: 0.05 μg each of recombinant AFP-L3 (lane 1), non-fucosylated AFP (lane 2), fucosylated ALP (lane 3)

Primary antibody: S4-1F8, S4-4F9 (10-fold diluted hybridoma culture supernatant) 4° C. O/N Secondary antibody: the following two-kind mixing RT 1 hr anti mouse-IgG (Fc) Ab-HRP (BET/cat # A90-131P) (20,000-fold dilution)

anti mouse-IgM Ab-HRP (SBA/cat#1020-05) (5,000-fold dilution)

<Method>

(1) Add ¼ volume of NuPAGE LDS Sample Buffer (4×) (Thermo/NP0008) to each antigen and ⅒ volume of NuPAGE Sample Reducing Agent (10×) (Thermo/NP0009) and mix.

(2) Subject a molecular weight marker and each antigen of (1) to electrophoresis (SDS-PAGE).

(3) Perform blotting on a PVDF membrane.

(4) Block by immersing in PVDF Blocking Reagent for Can Get Signal at room temperature for 1 hour.

(5) Wash 3 times with TBST.

(6) Dilute the primary antibody to the following dilution ratio with 1% BSA-TBST and react at 4° C. overnight.

(7) Wash 3 times with TBST.

(8) Dilute the secondary antibody to the dilution ratio described in the <Materials> with 1% BSA-TBST, and react at room temperature for 1 hour.

(9) Wash 3 times with TBST.

(10) Detect by chemiluminescence.

<Results>

Figure 4:
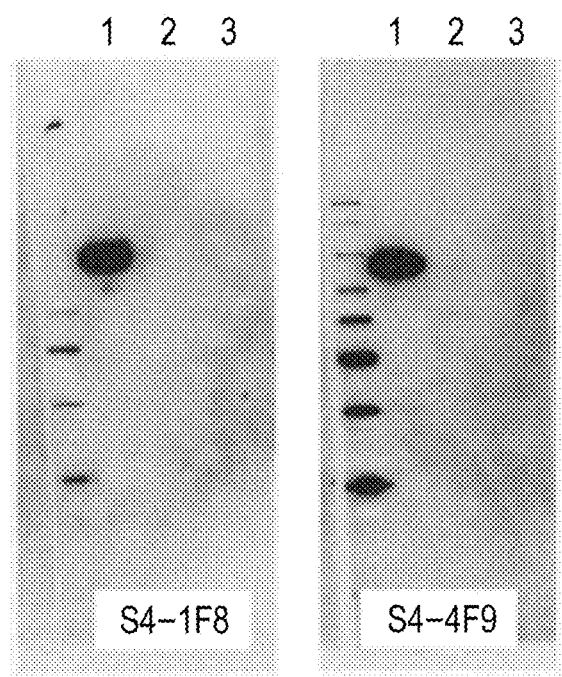
FIG. 4 is a diagram showing the result of western blotting of the clones S4-1F8 and S4-4F9 obtained in Example 1 (lane 1: fucosylated AFP (AFP-L3/recombinant) (positive antigen), lane 2: non-fucosylated AFP (LCA lectin non-adsorbed fraction of human serum-derived AFP (LEE biosolutions) (negative antigen), and lane 3: fucosylated ALP (oriental yeast/47787055) (negative antigen))

The results of western blotting are shown in FIG. 4. Both S4-1F8 and S4-4F9 showed a reaction only to AFP-L3.

(3) Confirmation of Epitope

In order to investigate the epitope range of antibodies S4-1F8 and S4-4F9, the following investigations were carried out.

<Materials>

Solid phase antigen: glycopeptides (SEQ ID NOs: 18 to 25) shown in FIG. 9 were used (Fuc+, Fuc−)

Primary antibody: S4-1F8, S4-4F9 (hybridoma culture supernatant)

Secondary antibody: anti mouse IgG-HRP (MEDICAL & BIOLOGICAL LABORATORIES CO., LTD./IM-0817)

<Method>

(1) Add 100 μl/well of 2 μg/ml each antigen (10 mM tris buffer dilution pH 7.4) to a 96-well plate (nunc Maxisoap/446612) and immobilize the antigen at RT for 1 hr.

(2) Wash each well with 300 μl/well TBST×5 times.

(3) Block each well with 300 μl/well 1% BSA-TBS at 4° C. overnight.

(4) Wash each well with 300 μl/well TBST×5 times.

(5) Dilute antibody culture supernatant (primary antibody) 10 times with 1% BSA-TBST, add 100 μl/well, and react at RT for 1 hour.

(6) Wash each well with 300 μl/well TBST×5 times.

(7) Dilute the secondary antibody 10,000 times with 1% BSA-TBST, add 100 μl/well, and react at RT for 0.5 hr.

(8) Wash each well with 300 μl/well TBST×5 times.

(9) Add 100 μl/well of HRP chromogenic substrate to develop color.

(10) Add 100 μl/well of a stop solution to stop color development.

(11) Measure OD450.

<Results>

Figure 5:
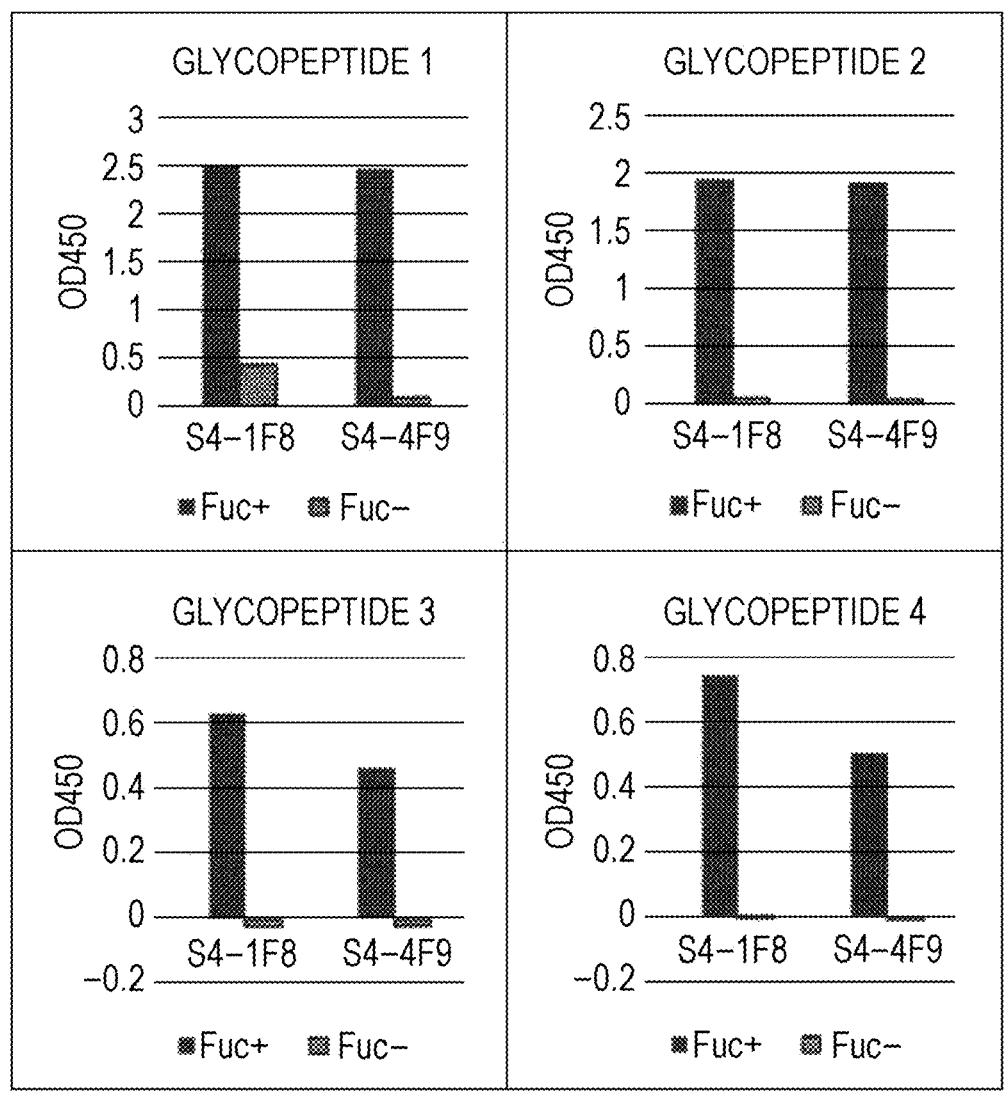
FIG. 5 is a diagram showing the result of performing antigen solid phase ELISA using positive glycopeptide (Fuc+) and negative glycopeptide (Fuc−) as antigens.

The results of antigen solid phase ELISA are shown in FIG. 5. S4-1F8 and S4-4F9 showed reactivity to any of the positive glycopeptides (Fuc+) and showed no reactivity to the negative glycopeptides (Fuc−).

It is suggested that fucose is contained in the epitope since the reactivity markedly varies depending on the presence or absence of fucose in any of the glycopeptides.

It is suggested that not only fucose but also peptide moiety is contained in the epitope since the antibodies did not show reactivity to another protein with fucose (ALP). The epitope of the peptide moiety is considered to be contained in "TKVNFT") (SEQ ID NO: 14) since the antibodies also reacted to the shortest glycopeptide (7a.a. trisaccharide) of the peptide chain.

(4) Confirmation of CDR Sequence

CDR analysis of S4-1F8 and S4-4F9 was performed. The CDR sequences (SEQ ID NOs: 1 to 6) of the S4-1F8 antibody are shown in Table 4. The CDR sequences (SEQ ID NOs: 7 to 12) of the S4-4F9 antibody are shown in Table 5.

TABLE 4

|  | Heavy chain | Light chain |
| --- | --- | --- |
| CDR1 | GFNIKDYY | GNIHNY |
| CDR2 | IDPEDGES | DAK |
| CDR3 | ARPLYSTYDVDWYFDV | QHFWTTPLT |

TABLE 5

|  | Heavy chain | Light chain |
| --- | --- | --- |
| CDR1 | GFNIKDYY | GNIHNY |
| CDR2 | IDPEDGES | DVK |
| CDR3 | ARPLYSTYDFDWYFDV | QHFWTTPLT |

Example 3

Construction of Sandwich ELISA and its Effect on Reactivity by SDS:

By using S4-1F8 or S4-4F9 obtained in Example 1, construction of a sandwich ELISA was attempted as follows. The effect on reactivity by SDS was investigated.

<Materials>

Antibody-sensitized plates (S4-1F8, S4-4F9/2.5 μg/mL 100 μL/well) recombinant AFP-L3 antigen Anti-AFP antibody: Polyclonal Antibody to Alpha-Fetoprotein(WLS/# PAA153Hu01)

Labeled antibody: Goat anti rabbit immunoglobulin-HRP

Buffer A: 150 mM NaCl+1% BSA/10 mM phosphate buffer (pH7)

Buffer B: 150 mM NaCl+0.05% Tween 20/10 mM phosphate buffer (pH7)

<Method>

(1) (Antigen pretreatment) Add an equal amount of 2%, 1%, 0.5%, 0.25%, 0.13%, 0.06% SDS solution to 20 μg/mL AFP-L3 antigen solution, then leave the mixed solutions for 3 minutes or more. (Pretreatment SDS concentration: 0.03 to 1%)

(2) Dilute the mixed solutions with Buffer A so that the antigen concentrations are 1 μg/mL, 0.5 μg/mL, 0.25 μg/mL. (Final SDS concentration: 0.00075% to 0.1%)

(3) Add 100 μL/well of the antigen solution to an antibody-sensitized plate and react at room temperature for 60 minutes.

(4) After washing each well with Buffer B, add 100 μL/well of 400-fold diluted anti-AFP antibody, and react at room temperature for 60 minutes.

(5) After washing each well with Buffer B, add 100 μL/well of 4000-fold diluted labeled antibody, and react at room temperature for 40 minutes.

(6) After washing each well with Buffer B, add 100 μl/well of HRP chromogenic substrate to develop color for 20 minutes.

(7) Add 100 μl/well of a stop solution to stop color development and measure OD450.

<Results>

The measured values of OD450 at various antigen concentrations, final SDS concentrations, and pretreatment SDS concentrations in the case of using S4-1F8 are shown in Table 6. The measured values of OD450 at various antigen concentrations, final SDS concentrations, and pretreatment SDS concentrations in the case of using S4-4F9 are shown in Table 7.

antibody reaction was 0.05% or less, and a stronger signal was detected under the condition of 0.025% or less.

Example 4

Confirmation of Specificity of Sandwich ELISA:

Specificity of the sandwich ELISA using S4-1F8 constructed in Example 3 was confirmed as follows.

<Materials>

Antibody-sensitized plate (S4-1F8/2.5 μg/mL 100 μL/well)

Positive antigen: recombinant AFP-L3 antigen

Negative antigen 1: non-fucosylated AFP (LCA lectin non-adsorbed fraction of human serum-derived AFP (LEE biosolutions))

Negative antigen 2: fucosylated protein ALP (Oriental yeast) other than AFP

Biotinylated anti-AFP antibody: anti AFP, Human (mouse) (ABV/H00000174-M01)

Detection reagent: HRP-Conjugated Streptavidin (Thermo/N100)

Buffer A: 150 mM NaCl+1% BSA/10 mM phosphate buffer (pH7)

Buffer B: 150 mM NaCl+0.05% Tween 20/10 mM phosphate buffer (pH7)

<Method>

(1) Add (denaturation) or not add (non denaturation) an equal amount of a 0.06% SDS solution to each 20 μg/mL antigen solution, then leave the mixed solution for 3 minutes or more. (Pretreatment SDS concentration: 0.03%)

TABLE 6

| Final SDS concentration | Antigen: 1 μg/mL | | Antigen: 0.5 μg/mL | | Antigen: 0.25 μg/mL | |
|---|---|---|---|---|---|---|
| | Pretreatment SDS Concentration | OD450 | Pretreatment SDS Concentration | OD450 | Pretreatment SDS Concentration | OD450 |
| 0.1% | 1% | 0.83 | — | — | — | — |
| 0.05% | 0.5% | 1.29 | 1% | 1.00 | — | — |
| 0.025% | 0.25% | 2.06 | 0.5% | 1.65 | 1% | 1.21 |
| 0.013% | 0.125% | 1.95 | 0.25% | 1.44 | 0.5% | 1.10 |
| 0.006% | 0.06% | 1.83 | 0.125% | 1.29 | 0.25% | 0.94 |
| 0.003% | 0.03% | 1.84 | 0.06% | 1.28 | 0.125% | 0.88 |
| 0.0015% | — | — | 0.03% | 1.35 | 0.06% | 0.85 |
| 0.00075% | — | — | — | — | 0.03% | 0.90 |

TABLE 7

| Final SDS concentration | Antigen: 1 μg/mL | | Antigen: 0.5 μg/mL | | Antigen: 0.25 μg/mL | |
|---|---|---|---|---|---|---|
| | Pretreatment SDS Concentration | OD450 | Pretreatment SDS Concentration | OD450 | Pretreatment SDS Concentration | OD450 |
| 0.1% | 1% | 0.76 | — | — | — | — |
| 0.05% | 0.5% | 1.26 | 1% | 1.07 | — | — |
| 0.025% | 0.25% | 1.92 | 0.5% | 1.46 | 1% | 1.18 |
| 0.013% | 0.125% | 2.00 | 0.25% | 1.26 | 0.5% | 1.11 |
| 0.006% | 0.06% | 1.95 | 0.125% | 1.43 | 0.25% | 0.99 |
| 0.003% | 0.03% | 2.06 | 0.06% | 1.40 | 0.125% | 1.01 |
| 0.0015% | — | — | 0.03% | 1.45 | 0.06% | 1.00 |
| 0.00075% | — | — | — | — | 0.03% | 0.99 |

A signal was measured at any SDS concentration, and AFP-L3 was detected. A strong signal was detected under the condition that the SDS concentration in the antigen- (2) Dilute the mixed solutions with Buffer A so that the antigen concentrations are 1000 ng/mL, 500 ng/mL, 250 ng/mL, 125 ng/mL, 63 ng/mL, 31 ng/mL.

(3) Add 100 μL/well of the antigen solution to an antibody-sensitized plate and react at room temperature for 60 minutes.

(4) Wash each well with Buffer B, add 100 μL/well of 480-fold diluted biotinylated anti-AFP antibody, and react at room temperature for 60 minutes.

(5) After washing each well with Buffer B, add 100 μL/well of 10000-fold diluted detection reagent, and react at room temperature for 60 minutes.

(6) After washing each well with Buffer B, add 100 μl/well of HRP chromogenic substrate to develop color for 10 minutes.

(7) Add 100 μl/well of a stop solution to stop color development and measure OD450.

<Results>

The measured values of OD450 at various antigen concentrations in the case of using S4-1F8 are shown in Table 8.

TABLE 8

| Antigen concentration (ng/mL) | 1000 | 500 | 250 | 125 | 63 | 31 |
|---|---|---|---|---|---|---|
| Denatured AFP-L3 | * | * | 3.32 | 2.77 | 1.89 | 1.17 |
| Non-denatured AFP-L3 | 3.15 | 2.57 | 1.77 | 1.13 | 0.71 | 0.47 |
| Denatured AFP | 0.23 | 0.22 | 0.22 | 0.21 | 0.21 | 0.22 |
| Non-denatured AFP | 0.24 | 0.23 | 0.23 | 0.21 | 0.22 | 0.22 |
| Denatured ALP | 0.25 | 0.24 | 0.24 | 0.23 | 0.23 | 0.25 |
| Non-denatured ALP | 0.26 | 0.25 | 0.27 | 0.25 | 0.26 | 0.28 |

*No data since it exceeded the upper limit of measurement.

In either the denatured state or the non-denatured state, the S4-1F8 antibody showed no reaction to non-fucosylated AFP and ALP, whereas signal rise was seen in AFP-L3 in an antigen concentration-dependent manner. In particular, reactivity to AFP-L3 was markedly improved in the denatured state. From these facts, it was shown that the S4-1F8 antibody reacts specifically with AFP-L3 by sandwich ELISA by simultaneously recognizing fucose and peptide moiety of AFP-L3. In addition, it was shown that the antigen strongly reacts by pretreating with 0.03% SDS.

Example 5

Reactivity with Natural Human AFP-L3:

Whether S4-1F8 reacts with natural human AFP-L3 was confirmed by western blotting as follows.

<Materials>

Electrophoresis antigen: 50 ng of recombinant AFP-L3 (lane 1), 50 ng of non-fucosylated AFP (lane 2), 0.5 ng of calibrator 1 for μTAS Wako AFP-L 3 (lane 3), 0.5 ng of calibrator 2 for μTAS Wako AFP-L 3 (lane 4)

Primary antibody: S4-1F8 (10-fold diluted hybridoma culture supernatant) 4° C. O/N Secondary antibody: anti mouse-IgG (Fc) Ab-HRP (BET/# A90-131P) (20,000-fold dilution) RT 1 hr <Method>

Western blotting was carried out in the same manner as in (2) of Example 2 except that the electrophoresis antigen, the primary antibody, and the secondary antibody were replaced with the above.

<Results>

Figure 6:
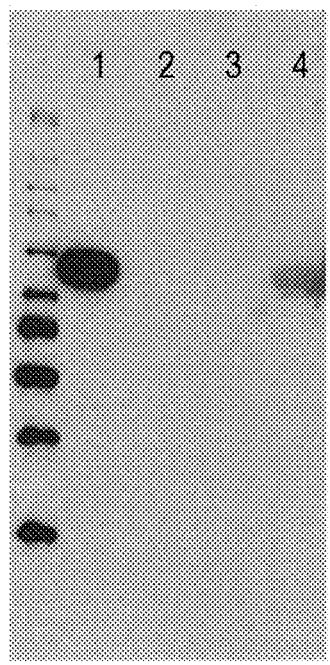
FIG. 6 is a diagram showing the result of western blotting of S4-1F8 (lane 1: recombinant AFP-L3, lane 2: non-fucosylated AFP, lane 3: natural human AFP (calibrator 1 for µTAS Wako AFP-L3), and lane 4: natural human AFP-L3 (calibrator 2 for µTAS Wako AFP-L3)).

The results of western blotting are shown in FIG. 6. S4-1F8 also showed a reaction to calibrator 2 for μTAS Wako AFP-L3, namely, natural human AFP-L3.

What is claimed is:

1. A method for detecting fucosylated α-fetoprotein (AFP), wherein said method comprises:
   mixing a sample obtained from a subject with a reagent comprising an antibody; and
   detecting fucosylated AFP by detecting an immunocomplex of fucosylated AFP and the antibody, wherein the antibody binds to a glycopeptide (a) (SEQ ID NO: 13),

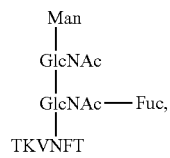

(a)

and
   does not bind to a glycopeptide (b) (SEQ ID NO: 14)

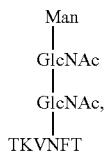

(b)

wherein the antibody is selected from the group consisting of (a) and (b):
   (a) an antibody that comprises a heavy chain variable region comprising: a complementarity determining region (CDR) comprising the amino acid sequence of SEQ ID NO: 1; a CDR comprising the amino acid sequence of SEQ ID NO: 2; and a CDR comprising the amino acid sequence of SEQ ID NO: 3,
   and wherein the antibody further comprises a light chain variable region comprising: a CDR comprising the amino acid sequence of SEQ ID NO: 4; a CDR comprising the amino acid sequence of SEQ ID NO: 5; and a CDR comprising the amino acid sequence of SEQ ID NO: 6, and
   (b) an antibody that comprises a heavy chain variable region comprising: a CDR comprising the amino acid sequence of SEQ ID NO: 7; a CDR comprising the amino acid sequence of SEQ ID NO: 8; and a CDR comprising the amino acid sequence of SEQ ID NO: 9,
   and wherein the antibody further comprises a light chain variable region comprising: a CDR comprising the amino acid sequence of SEQ ID NO: 10; a CDR comprising the amino acid sequence of SEQ ID NO: 11; and a CDR comprising the amino acid sequence of SEQ ID NO: 12.

2. The method of claim 1, comprising steps of pretreating the fucosylated AFP with a solution comprising SDS of 0.03 mass/mass % or more, and contacting the pretreated fucosylated AFP with the antibody, in the presence of SDS of 0.025 mass/mass % or less.

3. The method of claim 1, wherein the antibody comprises a heavy chain variable region comprising: a CDR comprising the amino acid sequence of SEQ ID NO: 1; a CDR comprising the amino acid sequence of SEQ ID NO: 2; and a CDR comprising the amino acid sequence of SEQ ID NO: 3,
   and wherein the antibody further comprises a light chain variable region comprising: a CDR comprising the amino acid sequence of SEQ ID NO: 4; a CDR comprising the amino acid sequence of SEQ ID NO: 5; and a CDR comprising the amino acid sequence of SEQ ID NO: 6.

4. The method of claim 1, wherein the antibody comprises a heavy chain variable region comprising: a CDR comprising the amino acid sequence of SEQ ID NO: 7; a CDR comprising the amino acid sequence of SEQ ID NO: 8; and a CDR comprising the amino acid sequence of SEQ ID NO: 9,
   and wherein the antibody further comprises a light chain variable region comprising: a CDR comprising the amino acid sequence of SEQ ID NO: 10; a CDR comprising the amino acid sequence of SEQ ID NO: 11; and a CDR comprising the amino acid sequence of SEQ ID NO: 12.

* * * * *

SEQUENCE LISTING

```
<160> NUMBER OF SEQ ID NOS: 26

<210> SEQ ID NO 1
<211> LENGTH: 8
<212> TYPE: PRT
<213> ORGANISM: Artificial Sequence
<220> FEATURE:
<223> OTHER INFORMATION: Synthetic CDR-A peptide sequence

<400> SEQUENCE: 1

Gly Phe Asn Ile Lys Asp Tyr Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic CDR-A peptide sequence

<400> SEQUENCE: 2

Ile Asp Pro Glu Asp Gly Glu Ser
1               5

<210> SEQ ID NO 3
<211> LENGTH: 16
<212> TYPE: PRT
<213> ORGANISM: Artificial Sequence
<220> FEATURE:
<223> OTHER INFORMATION: Synthetic CDR-A peptide sequence

<400> SEQUENCE: 3
```

```
Ala Arg Pro Leu Tyr Ser Thr Tyr Asp Val Asp Trp Tyr Phe Asp Val
1               5                   10                  15

<210> SEQ ID NO 4
<211> LENGTH: 6
<212> TYPE: PRT
<213> ORGANISM: Artificial Sequence
<220> FEATURE:
<223> OTHER INFORMATION: Synthetic CDR-A peptide sequence

<400> SEQUENCE: 4

Gly Asn Ile His Asn Tyr
1               5

<210> SEQ ID NO 5
<211> LENGTH: 3
<212> TYPE: PRT
<213> ORGANISM: Artificial Sequence
<220> FEATURE:
<223> OTHER INFORMATION: Synthetic CDR-A peptide sequence

<400> SEQUENCE: 5

Asp Ala Lys
1

<210> SEQ ID NO 6
<211> LENGTH: 9
<212> TYPE: PRT
<213> ORGANISM: Artificial Sequence
<220> FEATURE:
<223> OTHER INFORMATION: Synthetic CDR-A peptide sequence

<400> SEQUENCE: 6

Gln His Phe Trp Thr Thr Pro Leu Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic CDR-B peptide sequence

<400> SEQUENCE: 7

Gly Phe Asn Ile Lys Asp Tyr Tyr
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic CDR-B peptide sequence

<400> SEQUENCE: 8

Ile Asp Pro Glu Asp Gly Glu Ser
1               5

<210> SEQ ID NO 9
<211> LENGTH: 16
<212> TYPE: PRT
<213> ORGANISM: Artificial Sequence
<220> FEATURE:
<223> OTHER INFORMATION: Synthetic CDR-B peptide sequence

<400> SEQUENCE: 9

Ala Arg Pro Leu Tyr Ser Thr Tyr Asp Phe Asp Trp Tyr Phe Asp Val
```

```
1               5                   10                  15
```

<210> SEQ ID NO 10
<211> LENGTH: 6
<212> TYPE: PRT
<213> ORGANISM: Artificial Sequence
<220> FEATURE:
<223> OTHER INFORMATION: Synthetic CDR-B peptide sequence

<400> SEQUENCE: 10

Gly Asn Ile His Asn Tyr
1               5

<210> SEQ ID NO 11
<211> LENGTH: 3
<212> TYPE: PRT
<213> ORGANISM: Artificial Sequence
<220> FEATURE:
<223> OTHER INFORMATION: Synthetic CDR-B peptide sequence

<400> SEQUENCE: 11

Asp Val Lys
1

<210> SEQ ID NO 12
<211> LENGTH: 9
<212> TYPE: PRT
<213> ORGANISM: Artificial Sequence
<220> FEATURE:
<223> OTHER INFORMATION: Synthetic CDR-B peptide sequence

<400> SEQUENCE: 12

Gln His Phe Trp Thr Thr Pro Leu Thr
1               5

<210> SEQ ID NO 13
<211> LENGTH: 6
<212> TYPE: PRT
<213> ORGANISM: Artificial Sequence
<220> FEATURE:
<223> OTHER INFORMATION: synthetic glycopeptide represented by formula
      (a)
<220> FEATURE:
<221> NAME/KEY: CARBOHYD
<222> LOCATION: (4)..(4)

<400> SEQUENCE: 13

Thr Lys Val Asn Phe Thr
1               5

<210> SEQ ID NO 14
<211> LENGTH: 6
<212> TYPE: PRT
<213> ORGANISM: Artificial Sequence
<220> FEATURE:
<223> OTHER INFORMATION: synthetic glycopeptide represented by formula
      (b)
<220> FEATURE:
<221> NAME/KEY: CARBOHYD
<222> LOCATION: (4)..(4)

<400> SEQUENCE: 14

Thr Lys Val Asn Phe Thr
1               5

<210> SEQ ID NO 15
<211> LENGTH: 16
<212> TYPE: PRT

```
<213> ORGANISM: Artificial Sequence
<220> FEATURE:
<223> OTHER INFORMATION: synthetic glycopeptide represented by formula
      (c)
<220> FEATURE:
<221> NAME/KEY: CARBOHYD
<222> LOCATION: (5)..(5)

<400> SEQUENCE: 15

Ala Thr Lys Val Asn Phe Thr Glu Ala Gln Lys Ala Ala Leu Asp Val
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: synthetic glycopeptide A
<220> FEATURE:
<221> NAME/KEY: CARBOHYD
<222> LOCATION: (5)..(5)

<400> SEQUENCE: 16

Ala Thr Lys Val Asn Phe Thr Glu Ala Gln Lys Ala Ala Leu Asp Val
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: synthetic non-fucosylated glycopeptide A
<220> FEATURE:
<221> NAME/KEY: CARBOHYD
<222> LOCATION: (5)..(5)

<400> SEQUENCE: 17

Ala Thr Lys Val Asn Phe Thr Glu Ala Gln Lys Ala Ala Leu Asp Val
1               5                   10                  15

<210> SEQ ID NO 18
<211> LENGTH: 7
<212> TYPE: PRT
<213> ORGANISM: Artificial Sequence
<220> FEATURE:
<223> OTHER INFORMATION: synthetic glycopeptide Fuc+
<220> FEATURE:
<221> NAME/KEY: CARBOHYD
<222> LOCATION: (5)..(5)

<400> SEQUENCE: 18

Gly Thr Lys Val Asn Phe Thr
1               5

<210> SEQ ID NO 19
<211> LENGTH: 7
<212> TYPE: PRT
<213> ORGANISM: Artificial Sequence
<220> FEATURE:
<223> OTHER INFORMATION: synthetic glycopeptide Fuc-
<220> FEATURE:
<221> NAME/KEY: CARBOHYD
<222> LOCATION: (5)..(5)

<400> SEQUENCE: 19

Gly Thr Lys Val Asn Phe Thr
1               5

<210> SEQ ID NO 20
```

```
<211> LENGTH: 10
<212> TYPE: PRT
<213> ORGANISM: Artificial Sequence
<220> FEATURE:
<223> OTHER INFORMATION: synthetic glycopeptide Fuc+
<220> FEATURE:
<221> NAME/KEY: CARBOHYD
<222> LOCATION: (5)..(5)

<400> SEQUENCE: 20

Gly Thr Lys Val Asn Phe Thr Glu Ile Gln
1               5                   10

<210> SEQ ID NO 21
<211> LENGTH: 10
<212> TYPE: PRT
<213> ORGANISM: Artificial Sequence
<220> FEATURE:
<223> OTHER INFORMATION: synthetic glycopeptide Fuc-
<220> FEATURE:
<221> NAME/KEY: CARBOHYD
<222> LOCATION: (5)..(5)

<400> SEQUENCE: 21

Gly Thr Lys Val Asn Phe Thr Glu Ile Gln
1               5                   10

<210> SEQ ID NO 22
<211> LENGTH: 10
<212> TYPE: PRT
<213> ORGANISM: Artificial Sequence
<220> FEATURE:
<223> OTHER INFORMATION: glycopeptide Fuc+
<220> FEATURE:
<221> NAME/KEY: CARBOHYD
<222> LOCATION: (5)..(5)

<400> SEQUENCE: 22

Gly Thr Lys Val Asn Phe Thr Glu Ile Gln
1               5                   10

<210> SEQ ID NO 23
<211> LENGTH: 10
<212> TYPE: PRT
<213> ORGANISM: Artificial Sequence
<220> FEATURE:
<223> OTHER INFORMATION: synthetic glycopeptide Fuc-
<220> FEATURE:
<221> NAME/KEY: CARBOHYD
<222> LOCATION: (5)..(5)

<400> SEQUENCE: 23

Gly Thr Lys Val Asn Phe Thr Glu Ile Gln
1               5                   10

<210> SEQ ID NO 24
<211> LENGTH: 16
<212> TYPE: PRT
<213> ORGANISM: Artificial Sequence
<220> FEATURE:
<223> OTHER INFORMATION: synthetic glycopeptide Fuc+
<220> FEATURE:
<221> NAME/KEY: CARBOHYD
<222> LOCATION: (5)..(5)

<400> SEQUENCE: 24

Ala Thr Lys Val Asn Phe Thr Glu Ala Gln Lys Ala Ala Leu Asp Val
1               5                   10                  15
```

```
<210> SEQ ID NO 25
<211> LENGTH: 16
<212> TYPE: PRT
<213> ORGANISM: Artificial Sequence
<220> FEATURE:
<223> OTHER INFORMATION: synthetic glycopeptide Fuc-
<220> FEATURE:
<221> NAME/KEY: CARBOHYD
<222> LOCATION: (5)..(5)

<400> SEQUENCE: 25

Ala Thr Lys Val Asn Phe Thr Glu Ala Gln Lys Ala Ala Leu Asp Val
1               5                   10                  15

<210> SEQ ID NO 26
<211> LENGTH: 609
<212> TYPE: PRT
<213> ORGANISM: Homo sapiens
<300> PUBLICATION INFORMATION:
<308> DATABASE ACCESSION NUMBER: NM_001134
<309> DATABASE ENTRY DATE: 2016-09-10
<313> RELEVANT RESIDUES IN SEQ ID NO: (1)..(609)

<400> SEQUENCE: 26

Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
    50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
        115                 120                 125

Lys Lys Pro Thr Pro Ala Ser Ile Pro Leu Phe Gln Val Pro Glu Pro
    130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
        195                 200                 205

Val Thr Lys Glu Leu Arg Glu Ser Ser Leu Leu Asn Gln His Ala Cys
    210                 215                 220

Ala Val Met Lys Asn Phe Gly Thr Arg Thr Phe Gln Ala Ile Thr Val
225                 230                 235                 240
```

```
Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
            260                 265                 270

Asp Val Leu Asp Cys Leu Gln Asp Gly Glu Lys Ile Met Ser Tyr Ile
            275                 280                 285

Cys Ser Gln Gln Asp Thr Leu Ser Asn Lys Ile Thr Glu Cys Cys Lys
290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335

Arg Asp Phe Asn Gln Phe Ser Ser Gly Glu Lys Asn Ile Phe Leu Ala
            340                 345                 350

Ser Phe Val His Glu Tyr Ser Arg Arg His Pro Gln Leu Ala Val Ser
            355                 360                 365

Val Ile Leu Arg Val Ala Lys Gly Tyr Gln Glu Leu Leu Glu Lys Cys
            370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
                405                 410                 415

Gly Leu Phe Gln Lys Leu Gly Glu Tyr Tyr Leu Gln Asn Ala Phe Leu
            420                 425                 430

Val Ala Tyr Thr Lys Lys Ala Pro Gln Leu Thr Ser Ser Glu Leu Met
            435                 440                 445

Ala Ile Thr Arg Lys Met Ala Ala Thr Ala Ala Thr Cys Cys Gln Leu
            450                 455                 460

Ser Glu Asp Lys Leu Leu Ala Cys Gly Glu Gly Ala Ala Asp Ile Ile
465                 470                 475                 480

Ile Gly His Leu Cys Ile Arg His Glu Met Thr Pro Val Asn Pro Gly
                485                 490                 495

Val Gly Gln Cys Cys Thr Ser Ser Tyr Ala Asn Arg Arg Pro Cys Phe
            500                 505                 510

Ser Ser Leu Val Val Asp Glu Thr Tyr Val Pro Pro Ala Phe Ser Asp
            515                 520                 525

Asp Lys Phe Ile Phe His Lys Asp Leu Cys Gln Ala Gln Gly Val Ala
            530                 535                 540

Leu Gln Thr Met Lys Gln Glu Phe Leu Ile Asn Leu Val Lys Gln Lys
545                 550                 555                 560

Pro Gln Ile Thr Glu Glu Gln Leu Glu Ala Val Ile Ala Asp Phe Ser
                565                 570                 575

Gly Leu Leu Glu Lys Cys Cys Gln Gly Gln Glu Gln Glu Val Cys Phe
            580                 585                 590

Ala Glu Glu Gly Gln Lys Leu Ile Ser Lys Thr Arg Ala Ala Leu Gly
            595                 600                 605

Val
```